US006984741B2

(12) United States Patent
Mägerlein

(10) Patent No.: US 6,984,741 B2
(45) Date of Patent: Jan. 10, 2006

(54) 5-NITROBENZOFURANS

(75) Inventor: Wolfgang Mägerlein, Leverkusen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/642,947

(22) Filed: Aug. 18, 2003

(65) Prior Publication Data

US 2004/0034220 A1 Feb. 19, 2004

(30) Foreign Application Priority Data

Aug. 19, 2002 (DE) ............................... 102 37 819

(51) Int. Cl.
*C07D 307/78* (2006.01)

(52) U.S. Cl. ................................................... 549/466

(58) Field of Classification Search ................. 549/466

See application file for complete search history.

(56) References Cited

U.S. PATENT DOCUMENTS

| 3,558,667 A | 1/1971 | Mooradian | 260/346.2 |
| 5,854,282 A | 12/1998 | Mellin | 514/469 |
| 6,297,233 B1 | 10/2001 | Stein et al. | 514/212.03 |

FOREIGN PATENT DOCUMENTS

| EP | 471 609 | 2/1992 |
| EP | 1 116 719 | 7/2001 |
| JP | 54163597 | 12/1979 |
| JP | 2002-255954 | 3/2001 |
| WO | 9846561 | 10/1998 |
| WO | 00/47207 | 8/2000 |
| WO | 01/28974 | 4/2001 |

OTHER PUBLICATIONS

Suzuki, T 'Benzofuran derivatives. II. synthesis of 2,3-dihydrobenzofurans from ethyl 2-acylphenoxyacetates' CA 105:190808 (1986).*

Horaguchi, T et al 'Benzofuran derivatives. Part 3. the reactivities of the intermediates in benzofuran synthesis' CA 108:75142 (1988).*

P. Cagniant et al, "Chimie Organique—Contribution a L'Etude du Naphto-(2.3-B) Furanne et de son Analogue Selenie Le Naphto-(2.3-B0 Selenophene Naphtho(2,3-B) Furan and its Selenium Analog Naphtho(2,3-B) Selenohone", Comptes Rendus Hebdomadaires Des Seances de L'Academie des Sciences, Serie C: Sciences Chimiques, Gauthier-Villars. Montreuil, Fr. Bd. 276, Nr. 22, May 28, 1973, Seiten 1629-1631, XP009019118, Beispiel XII, Seite 1629, dritter Absatz (Verbindung (I) mit R=OCH(r2)COOH mit R2=N-Butyl).

Erlenmeyer EH et al: "Zur Kenntnis des 5-Aminocumarons" Helvetica Chimica Acta, Verlag Helvetica Chimica Acta,. Basel, CH, Bd. 31, 1948, Seiten 75-77, XP002009857 ISSN: 0018-019X *Beispiel III* .

Spyroudis et al: "Phenyliodoniophenolates from 1,2-Dihydroxybenzene Derivatives" Tetrahedron, Elsevier Science Publishers, Amsterdam, NL, Bd. 50, Nr. 39, 1994, Seiten 11541-11552, XP002910906 ISSN: 0040-4020 * Beispiel.4* .

L.J. Powers et al.: "Antibacterial Activity of Nitrobenzofuranes" J. Med. Chem., Bd. 4, Nr. 3, 1967, Seiten 441-444, XP002257497.

A. Mooradian et al.: "The Preparation of O-Aryl Oximes and their Conversion to Benzofurnaces" J. Heterocycl. Chem. Bd. 4, Nr. 3, 1967, Seiten 441-444, *Tabelle 2 * .

* cited by examiner

*Primary Examiner*—Amelia A. Owens
(74) *Attorney, Agent, or Firm*—Diderico van Eyl

(57) ABSTRACT

The present invention relates to 5-nitrobenzofurans, to a process for preparing 5-nitrobenzofurans, and to 5-nitro-2, 3-dihydrobenzofuran-3-ols, to a process for the preparation thereof and to intermediates.

10 Claims, No Drawings

5-NITROBENZOFURANS

BACKGROUND OF THE INVENTION

1. Field of the Invention

The present invention relates to 5-nitrobenzofurans, to a process for preparing 5-nitrobenzofurans, as well as to 5-nitro-2,3-dihydrobenzofuran-3-ols, to a process for the preparation thereof and to their intermediates.

2. Brief Description of the Invention

Benzofurans have acquired industrial importance in particular as intermediates for preparing medicaments. The benzofuran structure is found for example in anti-arrhythmic active ingredients such as, for example, amiodarone and bufuralol.

2-(n-butyl)-5-nitrobenzofuran is used as intermediate in the preparation of dronedarone (N-[2-(n-butyl)-3-[4-[3-(dibutylamino)propoxy]benzoyl]-5-benzofuranyl] methanesulfonamide), which likewise has anti-arrhythmic activity.

EP-A 0 471 609 describes a process for preparing 2-(n-butyl)-5-nitrobenzofuran which starts from 2-hydroxy-5-nitrobenzyl bromide. This involves reaction with triphenylphosphane initially to prepare 2-hydroxy-5-nitrobenzyltriphenyl-phosphonium bromide, which is acylated with pentanoyl chloride in the presence of an amine base and subsequently cyclized to 2-(n-butyl)-5-nitrobenzofuran. The disadvantages of this process are the costly precursor 2-hydroxy-5-nitrobenzyl bromide, the low yield and the large amounts of waste, in particular of triphenylphosphane oxide.

WO-A 01/28974 and WO-A 01/29019 disclose processes for preparing 5-nitrobenzofurans, starting from salicylaldehyde, and proceeding in a four-stage synthesis via 2-(2-formyl-4-nitrophenoxy) carboxylic acids as intermediates. The disadvantages of this process are the cost of salicylaldehyde, and the fact that the oxidation-sensitive aldehyde functionality is present in all intermediates.

In a further process disclosed in EP-A 1 116 719, 5-nitro-2(3H)-benzofuranone is reacted in the presence of pentanoic acid and pentanoic anhydride to give 3-(1-hydroxypentylidene)-5-nitro-2(3H)-benzofuranone which reacts under acidic conditions to give 2-(n-butyl)-5-nitrobenzofuran. The disadvantage of this process is that 5-nitro-2(3H)-benzofuranone is used as precursor, which makes industrial application uneconomic.

There was thus a continuing need to develop an efficient and widely applicable process for preparing 5-nitrobenzofuranones which both starts from low-cost, easily obtainable precursors and can easily be implemented industrially.

SUMMARY OF THE INVENTION

A process for preparing compounds of the formula (I) has now been found

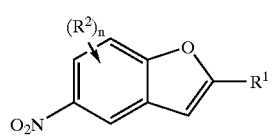

in which

R$^1$ is hydrogen or C$_1$–C$_{12}$-alkyl, and

R$^2$ are in each case independently of one another: fluorine, chlorine, bromine, iodine, C$_1$–C$_{12}$-alkyl, C$_1$–C$_{12}$-alkoxy, hydroxyl, NR$^3$R$^4$ or CONR$^3$R$^4$, where R$^3$ and R$^4$ are each, independently of one another, hydrogen or C$_1$–C$_{12}$-alkyl, or NR$^3$R$^4$ as a whole is a cyclic amino radical having 4 to 12 carbon atoms, COO—(C$_1$–C$_{12}$-alkyl), —COO(C$_4$–C$_{24}$-aryl), —COO(C$_5$–C$_{25}$-arylalkyl), CO(C$_1$–C$_{12}$-alkyl), CO(C$_4$–C$_{24}$-aryl) or C$_1$–C$_{1-2}$-fluoroalkyl and n is zero, one, two or three, or in the case where n is two or three it is possible for two adjacent R$^2$ substituents to be part of a fused ring system which in turn may optionally be substituted by the radicals mentioned above for R$^2$, which is characterized in that compounds of the formula (II)

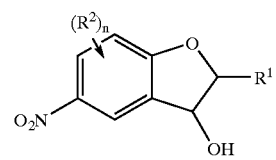

in which

R$^1$, R$^2$ and n have the meaning under formula (I), are converted by dehydration into compounds of the formula (I).

For the purposes of the invention it is possible for all the radical definitions, parameters and explanations which are general or specified in preferred ranges and are given above and detailed below to be combined with one another in any way, that is to say also between the respective ranges and preferred ranges.

DETAILED DESCRIPTION OF THE INVENTION

Alkyl or alkoxy is in each case independently a straight-chain, cyclic, branched or unbranched alkyl or alkoxy radical. The same applies to the nonaromatic part of an arylalkyl radical.

C$_1$–C$_4$-Alkyl is, for example, methyl, ethyl, n-propyl, isopropyl, n-butyl, sec-butyl and tert-butyl, C$_1$–C$_8$-alkyl is additionally, for example, n-pentyl, 1-methylbutyl, 2-methylbutyl, 3-methylbutyl, neopentyl, 1-ethylpropyl, cyclohexyl, cyclopentyl, n-hexyl, 1,1-dimethylpropyl, 1,2-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, 1-ethyl-2-methylpropyl, n-heptyl and n-octyl, and C$_1$–C$_{12}$-alkyl is furthermore, for example, adamantyl, the isomeric menthyls, n-nonyl, n-decyl and n-dodecyl.

C$_1$–C$_4$-Alkoxy is, for example, methoxy, ethoxy, n-propoxy, isopropoxy, n-butoxy, sec-butoxy and tert-butoxy, C$_1$–C$_8$-alkoxy is additionally n-pentoxy, 1-methylbutoxy, 2-methylbutoxy, 3-methylbutoxy, neopentoxy, 1-ethylpropoxy, cyclohexoxy, cyclopentoxy, n-hexoxy and n-octoxy, and $C_1-C_{12}$-alkoxy is furthermore, for example, adamantoxy, the isomeric menthoxy radicals, n-decoxy and n-dodecoxy.

Fluoroalkyl is in each case independently a straight-chain, cyclic, branched or unbranched alkyl radical which is substituted once, more than once or completely by fluorine atoms.

$C_1-C_{12}$-Fluoroalkyl is, for example, trifluoromethyl, 2,2,2-trifluoroethyl, pentafluoroethyl, nonafluorobutyl, heptafluoroisopropyl, perfluorooctyl and perfluorododecyl.

Aryl is in each case independently a heteroaromatic radical having 4 to 24 carbon atoms in the framework, in which zero, one, two or three carbon atoms in the framework of each ring, but at least one carbon atom in the framework of the whole molecule, can be replaced by hetero atoms selected from the group of nitrogen, sulphur or oxygen, but is preferably a carbocyclic aromatic radical having 6 to 24 carbon atoms in the framework.

Examples of carbocyclic aromatic radicals having 6 to 24 carbon atoms in the framework are phenyl, naphthyl, phenanthrenyl, anthracenyl or fluorenyl, and heteroaromatic radicals having 4 to 24 carbon atoms in the framework in which zero, one, two or three carbon atoms in the framework of each ring, but at least one carbon atom in the framework of the whole molecule, can be replaced by heteroatoms selected from the group of nitrogen, sulphur or oxygen are, for example, pyridinyl, oxazolyl, benzofuranyl, dibenzofuranyl or quinolinyl.

The carbocyclic aromatic radical or heteroaromatic radical may additionally be substituted by up to five identical or different substituents per ring, which are selected from the group of chlorine, fluorine, $C_1-C_{12}$-alkyl, $C_1-C_{12}$-alkoxy, di($C_1-C_8$-alkyl)amino, COO($C_1-C_8$-alkyl), CON($C_1-C_8$-alkyl)$_2$, COO($C_1-C_8$-arylalkyl), COO($C_4-C_{14}$-aryl), CO($C_1-C_8$-alkyl), $C_5-C_{15}$-arylalkyl or tri($C_1-C_6$-alkyl)siloxy.

$C_4-C_{24}$—Aryl is, for example, and preferably, phenyl, o-, p-, m-tolyl, o-, p-, m-anisyl, o-, p-, m-fluorophenyl, o-, p-, m-chlorophenyl, o-, p-, m-trifluoromethylphenyl, o-, p-, m-nitrophenyl and 2-, 3- and 4-pyridyl.

Arylalkyl is in each case independently a straight-chain, cyclic, branched or unbranched alkyl radical as defined above which can be substituted once, more than once or completely by aryl radicals as defined above.

$C_5-C_{15}$-Arylalkyl is, for example and preferably, benzyl or (R)- or (S)-1-phenylethyl.

The preferred substitution pattern for compounds of the formulae (I) and (II) is defined below:

$R^1$ is preferably hydrogen or $C_1-C_4$-alkyl and particularly preferably n-butyl.

$R^2$ is preferably in each case independently: fluorine, chlorine, $C_1-C_4$-alkyl, $C_1-C_4$-alkoxy, hydroxyl, COO—($C_1-C_4$-alkyl), trifluoromethyl, $NR^3R^4$ or $CONR^3R^4$, where $R^3$ and $R^4$ are each independently of one another hydrogen or $C_1-C_4$-alkyl, or $NR^3R^4$ as a whole is pyrrolidinyl or piperidinyl.

n is preferably zero or one, and more preferably zero.

The very particularly preferred compound of the formula (I) is 2-(n-butyl)-5-nitrobenzofuran.

Apart from 2-(n-butyl)-5-nitrobenzofuran, the compounds of the formula (I) are likewise included by the invention and represent starting materials for the development of new active ingredients for the treatment of cardiac arrhythmias.

The compounds of the formula (II) are also furthermore included by the invention. The very particularly preferred compound of the formula (II) is 2-(n-butyl)-5-nitro-2,3-dihydrobenzofuran-3-ol. Moreover, in the case of the compounds of the formula (II) where $R^1$ is not hydrogen, the (2R,3R); (2S,3S); (2S,3R) and (2R,3S) isomers each in pure form, and any mixtures of the isomers, are encompassed by the invention.

Particularly suitable dehydrating reagents, which may be employed in catalytic amounts where appropriate, for the purposes of the invention are: protic acids such as $H_2SO_4$ or $H_3PO_4$ or bisulphates such as $KHSO_4$, hydroxides such as NaOH and KOH, $P_2O_5$, $I_2$, and salts of zinc and copper such as, in particular, $CuSO_4$ and $ZnCl_2$. Protic acids are particularly preferred for the process of the invention. $H_2SO_4$ is very particularly preferred for the process of the invention.

The dehydration can be carried out in an organic solvent. Organic solvents preferably used are polar, protic and aprotic solvents. Polar solvents mean those having a dielectric constant at 25° C. of 5 or more. Organic solvents particularly preferred for the process of the invention are aliphatic $C_1-C_6$-alcohols. Ethanol is very particularly preferred for the process of the invention.

The dehydration can be carried out for example at temperatures from −20 to 150° C., preferably at 20 to 150° C., particularly preferably at 50 to 100° C. and very particularly preferably at 70 to 78° C.

The reaction may take for example from 0.5 to 20 hours, preferably 0.5 to 8 hours and particularly preferably from 4 to 5 hours.

The pressure during the reaction is not critical and can be, for example, 0.5 to 100 bar, preferably 0.8 to 10 bar. Ambient pressure is particularly preferred.

The compounds of the formula (II) can be obtained in a particularly advantageous manner by reducing compounds of the formula (III)

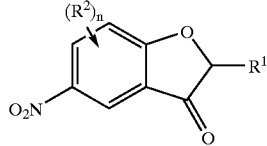

(III)

in which $R^1$, $R^2$ and n have the meanings specified under formula (I), including the preferred ranges.

Compounds of the formula (III) encompassed by the invention are those in which $R^2$ and n have the meanings specified under formula (I), including the preferred ranges, and $R^1$ is n-butyl. A particularly preferred compound of the formula (III) is 2-(n-butyl)-5-nitro-3(2H)-benzofuranone.

The compounds of the formula (III) can be reduced for example by transfer hydrogenation or by means of aluminium-hydrogen or boron-hydrogen compounds. The reduction is preferably effected by aluminium-hydrogen or boron-hydrogen compounds, particularly preferably by compounds of the formula (RI)

$$\text{Met}[EH_qR^5{}_{(4-q)}]_p \quad (RI)$$

in which

Met is a monovalent or divalent metal such as, preferably, zinc, lithium, sodium or potassium, and E is aluminium or boron and $R^5$ is $C_1-C_8$-alkyl, and q is 1, 2, 3 or 4, preferably 4 or 1 and p is the valency of Met, or by compounds of the formula (RII)

$$BH_rR^5_{(3-r)} \quad (RII)$$

in which
R⁵ has the meaning specified under formula (RI), and
r is one, two or three.

Very particularly preferred compounds of the formulae (RI) and (RII) are LiBH₄, NaBH₄, Zn(BH₄)₂, LiAlH₄, Li[BHEthyl₃] and Li[AlH(sec-butyl)₃], with NaBH₄ being even further preferred.

The amount of the aluminium-hydrogen or boron-hydrogen compounds is preferably chosen so that the molar ratio of hydrogen in the aluminium-hydrogen or boron-hydrogen compounds and the substrate is from 0.5 to 10, preferably 0.95 to 5 and particularly preferably 1.0 to 1.2. Larger ratios are possible but uneconomic.

Depending on the reagent employed, it is possible to employ polar solvents as solvents. The use of alkali metal boranates in aliphatic $C_1$–$C_6$-alcohols or ethers such as, in particular, 1,4-dioxane is preferred for the process of the invention. The reduction is very particularly preferably carried out with sodium borohydride in ethanol.

The reaction can be carried out for example at temperatures from −78 to 100° C., preferably 0 to 100° C. and particularly preferably 60 to 78° C.

The compounds of the formula (III) can be obtained in a particularly advantageous manner by nitration of compounds of the formula (IV)

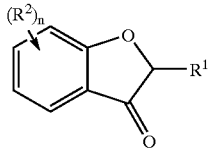

(IV)

in which R¹, R² and n have the meanings specified under formula (I), including the preferred ranges.

The reagents advantageously employed for the nitration are those able to generate nitrile cations (NO₂⁺). Nitric acid is preferred for example, preferably with a content of from 60 to 100% by weight based on HNO₃. The use of nitric acid, where appropriate as a mixture with sulphuric acid with a content of from 50 to 160% by weight based on H₂SO₄ and/or phosphoric acid with a content of from 70 to 160% by weight based on H₃PO₄, is likewise preferred. The use of nitrogen oxides such as NO₂, N₂O₃, N₂O₄, N₂O₅ or of NO is additionally preferred, where appropriate in the presence of an oxidizing agent. Preference is likewise given to nitration with nitrous acid HNO₂ or a salt of nitrous acid such as, in particular, NaNO₂, preferably in the presence of an oxidizing agent, or with ionic nitrile compounds such as, for example, NO₂⁺BF₄⁻. Alkyl nitrites of the general formula R⁶—ONO, where R⁶ is $C_1$–$C_{12}$-alkyl, are further preferably to be employed for the nitration.

The amount of nitration reagent employed is advantageously chosen so that the molar ratio of theoretically nitrating agent to compound of the formula (IV) is from 0.9 to 2, preferably 1.0 to 1.5 and particularly preferably 1.0 to 1.2.

A mixture of nitric acid with a content of from 60 to 100% by weight based on HNO₃ and sulphuric acid with a content of from 90 to 100% by weight based on H₂SO₄ is particularly preferably employed for the nitration.

Likewise particularly preferred for the nitration is nitric acid with a content of from 95 to 100% by weight.

In a preferred embodiment, the molar ratio of compound of the formula (IV) and nitric acid is between 0.9 and 1, particularly preferably between 0.95 and 1.05.

The nitration can be carried out for example with or without organic solvent, the organic solvent necessarily being inert under reaction conditions. Representatives of such organic solvents which may be particularly mentioned are halogenated aliphatic hydrocarbons such as, in particular, chlorinated aliphatic hydrocarbons such as, for example, dichloromethane, 1,2-dichloroethane, tetrachloromethane and hexachloroethane. Dichloromethane is preferred for the nitration of compounds of the formula (IV).

However, the nitration is preferably carried out without organic solvent. The amount concentration of the compound of the formula (IV) in the reaction medium can be, for example, from 0.2 to 3 mol/l, and from 0.3 to 1.6 mol/l is preferred.

The nitration can be carried out for example in a temperature range from −10 to 50° C., preferably between −10 and 20° C., particularly preferably between −5 to 10° C.

The process of the invention can be carried out under an inert gas atmosphere at atmospheric pressure, with the procedure possibly being for example as follows: for example it is possible to introduce the sulphuric acid first and then to meter in the compound of the formula (IV) and the nitric acid or a mixture of nitric acid and sulfuric acid. A further possibility is also for the nitric acid and the sulphuric acid to be introduced first and then the compound of the formula (IV) to be added, preferably in portions.

The reaction may take, depending on the amount employed, for example and preferably from 0.1 to 10 hours.

The product can be isolated by using the techniques which are customary in nitration reactions and are known to the skilled person. It is preferred for the process of the invention to transfer the reaction mixture to ice or ice-water and then filter or extract.

The compounds of the formula (IV) can be obtained in a preferred manner by hydrolysing compounds of the formula (V)

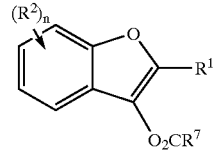

(V)

in which
R¹, R² and n have the meaning specified under formula (I), including the preferred ranges, and
R⁷ is $C_1$–$C_{12}$-alkyl, $C_5$–$C_{25}$-arylalkyl, $C_4$–$C_{24}$-aryl or $C_1$–$C_{12}$-fluoroalkyl,
R⁷ is preferably $C_1$–$C_4$-alkyl and particularly preferably methyl.

The hydrolysis can in this case be carried out with acids, bases, metal ions, enzymes or nucleophiles, where appropriate in catalytic amounts, and where appropriate in the presence of an organic solvent.

Preferably employed are bases such as, for example, aqueous amines such as, in particular, aqueous ammonia, hydroxides or carbonates such as, in particular, NaOH and KOH or acids such as, for example, aqueous hydrochloric acid, sulphuric acid, phosphoric acid, bisulphates, carboxylic acids such as, for example, formic acid or acetic acid, and sulphonic acids such as, for example, methanesulphonic acid or para-toluenesulfonic acid in various concentrations.

Acids are particularly preferably employed, very particularly preferably hydrochloric acid, sulphuric acid, or phosphoric acid, with 6N hydrochloric acid being even further preferred.

The acid is in this case preferably employed in amounts such that the molar ratio of compounds of the formula (V) to acid is from 1:1 to 1:100, preferably 1:1.1 to 1:10 and particularly preferably 1:5 to 1:6.

It is possible in a preferred embodiment to employ an organic solvent to improve the solubility of the compounds of the formula (V). Vigorous stirring and the use of ultrasound or of phase-transfer catalysts is also possible in addition. Preferred organic solvents are aliphatic $C_1$–$C_6$-alcohols or cyclic ethers. Ethanol is particularly preferably employed.

The reaction can be carried out at temperatures from 25 to 200° C., preferably at 60 to 100° C., particularly preferably at 70 to 78° C.

The reaction may last for example from 0.5 to 24 hours, and 1 to 6 hours are preferred.

The compounds of the formula (V) encompassed by the invention are those in which $R^2$ and n have the meanings specified under formula (I), including the preferred ranges, $R^7$ has the abovementioned meaning, including the preferred ranges thereof, and $R^1$ is n-butyl. A particularly preferred compound of the formula (V) is 3-acetoxy-2-(n-butyl)benzofuran.

The compounds of the formula (V) can be obtained in a particularly advantageous manner by cyclizing decarboxylation of compounds of the formula (VI)

(VI)

in which $R^1$, $R^2$ and n have the meanings specified under formula (I), including the preferred ranges, in the presence of at least one compound of the formula (RIII)

(RIII)

in which
R$^7$ has the meaning specified under formula (V), including the preferred ranges, and
R$^8$ is —O$_2$CR$^7$, hydroxyl or OM, where M is an alkaline earth metal or alkali metal.

The reaction is preferably carried out in the presence of a mixture of compounds of the formula (RIII), employing in each case an anhydride, preferably a homoanhydride (R$^7$CO)$_2$O, an alkali metal salt and a free acid. The R$^7$ radicals in the said compounds are preferably identical in each case. It is particularly preferred to employ mixtures of sodium acetate, acetic acid and acetic anhydride. The ratio of the amount of substances in this case is preferably (0.8 to 1.5):(2 to 4):(3 to 8), particularly preferably about 1:3:5.

The reaction temperature can be for example from 20 to 150° C., preferably 60 to 150° C. and particularly preferably 120 to 140° C.

The compounds of the formula (VI) can be obtained in a preferred manner by hydrolysing compounds of the formula (VII)

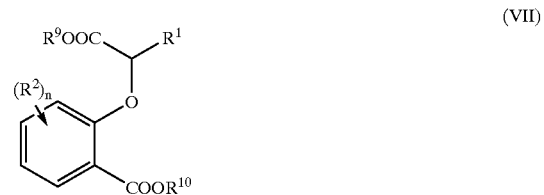

(VII)

in which
$R^1$, $R^2$ and n have the meanings specified under formula (I), including the preferred ranges, and
$R^9$ and $R^{10}$ are each independently of one another $C_1$–$C_{12}$-alkyl, $C_5$–$C_{25}$-arylalkyl or $C_4$–$C_{24}$-aryl, and not more than one $R^9$ or $R^{10}$ radical can be hydrogen.

$R^9$ and $R^{10}$ are preferably each independently of one another $C_1$–$C_4$-alkyl, particularly preferably each independently of one another methyl or ethyl and very particularly preferably each identically methyl or ethyl.

The hydrolysis can in this case be carried out with acids, bases, metal ions, enzymes or nucleophiles, where appropriate in catalytic amounts, and where appropriate in the presence of an organic solvent.

Bases such as, for example, aqueous amines such as, in particular, aqueous ammonia, hydroxides such as, in particular, LiOH, NaOH, KOH and Ca(OH)$_2$, carbonates such as Na$_2$CO$_3$, K$_2$CO$_3$ or CaCO$_3$ or aqueous acids such as, for example, hydrochloric acid, sulphuric acid, phosphoric acid, bisulphates, carboxylic acids such as, for example, formic acid or acetic acid, and sulphonic acids such as, for example, methanesulphonic acid or para-toluenesulfonic acid are preferably employed.

In a preferred embodiment, the hydrolysis is carried out in the presence of bases, with the use of LiOH, NaOH, KOH or Ca(OH)$_2$ being preferred. It is particularly preferred to use sodium hydroxide solution with a content of from 5 to 25% by weight. It is furthermore possible in a preferred embodiment to employ an organic solvent to improve the solubility of the compounds of the formula (VII).

For efficient hydrolysis of the ester groups, the base is preferably employed in amounts such that the molar ratio of base to compounds of the formula (VII) is from 1.5:1 to 20:1, preferably 2:1 to 7:1 and particularly preferably 3:1 to 5:1.

An organic solvent can be employed to improve the solubility of the substrate. Vigorous stirring and the use of ultrasound or of phase-transfer catalysts is additionally possible. The organic solvents preferably used for the process of the invention are aliphatic $C_1$–$C_6$-alcohols or cyclic ethers. Methanol or ethanol is particularly preferably employed.

The reaction can be carried out at temperatures from 20 to 200° C., preferably at 40 to 75° C. and particularly preferably at 40 to 60° C.

Compounds of the formula (VII) encompassed by the invention are those in which $R^2$ and n have the meanings specified under formula (I), including the preferred ranges, $R^9$ and $R^{10}$ then have the abovementioned meaning, including the preferred ranges thereof, and $R^1$ is n-butyl. Compounds of the formula (VII) which may be mentioned are:

methyl 2-(1-methoxycarbonylpentoxy)benzoate, ethyl 2-(1-methoxycarbonylpentoxy)benzoate, ethyl 2-(1-ethoxycarbonylpentoxy)benzoate and methyl 2-(1-ethoxycarbonylpentoxy)benzoate, 2-(1-methoxycarbonylpentoxy)benzoic acid, 2-(1-ethoxycarbonylpentoxy)benzoic acid, ethyl 2-(1-carboxypentoxy) benzoate and methyl 2-(1-carboxypentoxy)benzoate, and methyl 2-(1-methoxycarbonylhexoxy) benzoate, ethyl 2-(1-methoxycarbonylhexoxy)benzoate, ethyl 2-( 1-ethoxycarbonylhexoxy)benzoate and methyl 2-(1-ethoxycarbonylhexoxy) benzoate, 2-(1-methoxycarbonylhexoxy)benzoic acid, 2-(1-ethoxycarbonylhexoxy)benzoic acid, ethyl 2-(1-carboxyhexoxy)benzoate and methyl 2-( 1-carboxyhexoxy)benzoate.

The compounds of the formula (VII) can be obtained in a preferred manner by reacting compounds of the formula (VIII)

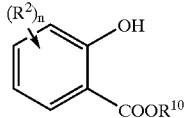

(VIII)

in which
  $R^2$ and n have the meanings specified under formula (I), including the preferred ranges, and
  $R^{10}$ is hydrogen, $C_1$–$C_{12}$-alkyl, $C_5$–$C_{25}$-arylalkyl or $C_4$–$C_{24}$-aryl, with compounds of the formula (IX)

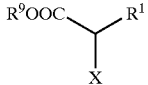

(IX)

in which
  $R^1$ has the meanings specified under formula (I), including the preferred ranges,
  $R^9$ is hydrogen, $C_1$–$C_{12}$-alkyl, $C_5$–$C_{25}$-arylalkyl or $C_4$–$C_{24}$-aryl, and
  X is chlorine, bromine, iodine or $R^{11}SO_3$— where $R^{11}$ is $C_1$–$C_{12}$-alkyl, $C_4$–$C_{24}$-aryl, $C_5$–$C_{25}$-arylalkyl or $C_1$–$C_{12}$-fluoroalkyl.
  $R^{11}$ is preferably $C_1$–$C_4$-alkyl or $C_4$–$C_{24}$-aryl, particularly preferably methyl, ethyl, phenyl, o-, m- or p-tolyl or trifluoromethyl.
  X is preferably chlorine or bromine, particularly preferably bromine.

The compounds of the formula (VIII) which are preferably employed are methyl o-hydroxybenzoate and ethyl o-hydroxybenzoate.

The compounds of the formula (IX) which are preferably employed are the methyl or ethyl 2-bromo carboxylates such as, in particular, methyl or ethyl 2-bromohexanoate.

The reaction of compounds of the formula (VIII) with compounds of the formula (IX) to give compounds of the formula (VII) is preferably carried out in the presence of base. A possible alternative to this is for the compound of the formula (VIII) first to be converted into the corresponding phenolate and be employed as such in the reaction.

The reaction can be carried out in an organic solvent. Reaction in water in the presence of a phase-transfer catalyst is also furthermore possible. Polar protic or aprotic solvents are preferably employed for the process of the invention, such as, for example, ketones such as acetone, amides such as N,N-dimethylformamide or N,N-dimethylacetamide, lactams such as 1,-methyl-2-pyrrolidinone, ethers such as tetrahydrofuran or dioxane, nitriles such as acetonitrile or benzonitrile or alcohols such as methanol or ethanol. Even further preferred for the process of the invention are acetone or acetonitrile.

The reaction can, where appropriate, be carried out under an inert gas atmosphere, for example an argon atmosphere.

The bases employed are those which are able at least partly to deprotonate the compounds of the formula (VIII) on the phenol function.

Inorganic bases or organic bases for example can be employed. Organic bases which can preferably be used are tertiary amines such as triethylamine or alkali metal alcoholates such as sodium methoxide or ethoxide, an inorganic base is for example alkali metal or alkaline earth metal hydroxides, carbonates or bicarbonates. Preferred bases are alkali metal carbonates, especially potassium carbonate or sodium carbonate.

The ratio of the amounts of the compounds of the formula (IX) employed and of the compounds of the formula (VIII) is advantageously chosen so that it is between 1.0 and 1.2.

The ratio of amounts between the base employed and the compound of the formula (VIII) employed is advantageously chosen between 1.0 and 1.5, with a ratio between 1.1 and 1.3 being preferred.

The reaction can be carried out for example at temperatures from 0 to 150° C., with preferred reaction temperatures being from 50 to 100° C., particularly preferably 70 to 80° C.

The compounds of the general formula (VI) may, where appropriate, also be prepared directly, without isolating the compounds of the formula (VII), by reacting compounds of the formula (VIII) with compounds of the formula (IX) in a one-pot process with hydrolysis of the ester functions taking place simultaneously.

An alternative possibility is also to prepare compounds of the formula (VI) by reacting those compounds of the formula (VIII) with those compounds of the formula (IX) in which $R^9$ and $R^{10}$ are each hydrogen. The amount of base is advantageously increased appropriately in this reaction.

The invention encompasses, besides a process for preparing compounds of the formula (I) from compounds of the formula (II), also processes for preparing compounds of the formula (I) from compounds of the formula (III), (IV), (V), (VI), (VII), (VIII) and (IX), each of which proceed via the described intermediates. The invention further encompasses processes for preparing compounds of the formula (II) from compounds of the formula (III) and, in each case, from the compounds (IV), (V), (VI), (VII), (VIII) and (IX), each of which proceed via the described intermediates.

The invention further encompasses processes for preparing compounds of the formula (III) from compounds of the formula (IV) and, in each case, from the compounds (V), (VI), (VII), (VI) and (IX), each of which proceed via the described intermediates.

The compounds of the formulae (I), (II) and (III) prepared according to the invention are particularly suitable for producing medicaments and physiologically active substances and for use in a process for producing medicaments and physiologically active substances.

Preferred medicaments and physiologically active substances in this connection are those employed for treating cardiac arrhythmias. A particularly preferred physiologically active substance is dronedarone.

The invention is distinguished through the fact that 5-nitrobenzofurans, 5-nitro-2,3-dihydrobenzofuran-3-ols and 5-nitro-3(2H)-benzofuranones can be obtained by a highly efficient and economic route, and synthetic processes for a wide spectrum of potential development candidates are disclosed.

The invention is further described by the following illustrative but non-limiting examples.

EXAMPLES

Example 1

Synthesis of Methyl 2-(1-methoxycarbonylpentoxy)benzoate 15.2 g of methyl salicylate and 18.0 g of potassium carbonate were introduced into 125 ml of acetonitrile in a 250 ml flask under an argon atmosphere and, at room temperature, 20.9 g of methyl 2-bromohexanoate were added. The colourless suspension was heated under reflux with stirring for 16 hours, and the progress of the reaction was checked by thin-layer chromatography. After cooling to room temperature, the suspension was filtered and the residue was washed with acetone. Concentration of the filtrate in vacuo resulted in 27.8 g (99% of theory) of methyl 2-(1-methoxycarbonylpentoxy)benzoate as yellow oil.

Example 2

Synthesis of 2-(1-carboxypentoxy)benzoic Acid 13.0 g of methyl 2-(1-methoxycarbonylpentoxy)benzoate were dissolved in methanol in a 250 ml flask, and a solution of 9.1 g of sodium hydroxide in 40 ml of water was added. The reaction mixture was stirred at 40° C. for one hour, during which a precipitate formed. This was dissolved after cooling to room temperature by adding further methanol and sodium hydroxide solution. The reaction mixture was washed with dichloromethane, and the aqueous phase was subsequently adjusted to pH 0 with concentrated hydrochloric acid while cooling in ice. A colourless solid precipitated during this and was filtered off and dried. 10.1 g (87% of theory) of 2-(1-carboxypentoxy)benzoic acid were obtained in this way.

Example 3

Synthesis of 3-acetoxy-2-(n-butyl)benzofuran 5.0 g of 2-(1-carboxypentoxy)benzoic acid and 1.6 g of sodium acetate were introduced into a 25 ml flask, and 3.4 ml of glacial acetic acid and 9.4 ml of acetic anhydride were added. The colourless suspension was heated to reflux for 4 hours.

Cooling, transferring the reaction mixture into ice-water, extracting with dichloromethane, drying the combined organic phases over sodium sulphate and removing the solvent resulted in a yellow oil in which, according to GC, the precursor and the product were present in an approximate ratio (percentage areas) of 50:50.

This oil was again mixed with 1.6 g of sodium acetate, 3.4 ml of glacial acetic acid and 9.4 ml of acetic anhydride and once more heated to reflux for 4 hours. Cooling and the same working up as described above resulted in 4.3 g (92% of theory) of 3-acetoxy-2-(n-butyl)benzofuran as pale yellow oil.

Example 4

Synthesis of 2-(n-butyl)-3(2H)-benzofuranone 4.6 g of 3-acetoxy-2-(n-butyl)benzofuran were dissolved in 20 ml of ethanol in a 100 ml flask, and 20 ml 6N hydrochloric acid were added. The mixture was heated to reflux for 4 hours. After cooling to room temperature, the pH was adjusted to 4 to 6 with sodium hydroxide, and the ethanol was distilled off. This was followed by extraction with dichloromethane. Drying of the combined organic phases over sodium sulphate and removal of the solvent resulted in 2.8 g (76% of theory) of 2-(n-butyl)-3(2H)-benzofuranone as yellow oil.

Example 5

Synthesis of 2-(n-butyl)-5-nitro-3(2H)-benzofuranone 2.9 ml of concentrated sulphuric acid were introduced into a 50 ml flask and cooled to 5° C. Then 1.0 g of 2-(n-butyl)-3(2H)-benzofuranone was slowly added, during which the reaction mixture assumed a brownish colour. It was stirred for 15 minutes. Subsequently, 0.7 g of nitration acid was slowly added dropwise in such a way that the temperature did not rise much above 5° C. The reaction mixture was then poured onto ice, stirred and extracted with dichloromethane. The dichloromethane extracts were washed with water, dried over sodium sulphate and evaporated to dryness in vacuo. The material (1.0 g) obtained in this way had, according to GC, a content of about 70% (percentage areas) of 2-(n-butyl)-5-nitro-3(2H)-benzofuranone. Further purification is possible by column chromatography (eluent: hexane:ethyl acetate=10:1).

$^1$H NMR (CDCl$_3$, 400 MHz): δ=8.49 (d, J=2.4 Hz, 1H, Ar—H), 8.45 (dd, J$_1$= 9.0 Hz, J$_2$=2.4 Hz, 1H, Ar—H), 7.17 (d, J=9.0 Hz, 1H, Aryl-H), 4.69 (dd, J$_1$= 8.0 Hz, J$_2$=4.4 Hz, 1H, O=C—CH), 2.0–1.9 (2×m, 2H, CH—CH$_2$), 1.40 (m, 2 H, CH$_2$), 1.33 (m, 2H, CH$_2$), 0.85 (t, J=7.2 Hz, 3H, CH$_3$).

Example 6

Synthesis of 2-(n-butyl)-5-nitro-2,3-dihydrobenzofuran-3-ol 700 mg of 2-(n-butyl)-5-nitro-3(2H)-benzofuranone were introduced into 10 ml of ethanol in a 50 ml flask and cooled to 0° C. A solution of 130 mg of NaBH$_4$ in 5 ml of ethanol was added dropwise thereto, an intense red coloration immediately appearing. The mixture was allowed to reach room temperature and was then briefly heated to reflux. After cooling to room temperature, the reaction mixture was taken up in water and dichloromethane, the organic phase was separated off, and the aqueous phase was extracted once more with dichloromethane. Drying of the combined organic phases over sodium sulphate, removal of the solvent in vacuo and column chromatography (eluent: hexane:ethyl acetate=5:1) resulted in 400 mg (57% of theory) of 2-(n-butyl)-5-nitro-2,3-dihydrobenzofuran-3-ol.

Example 7

Synthesis of 2-(n-butyl)-5-nitrobenzofuran 300 mg of 2-(n-butyl)-5-nitro-2,3-dihydrobenzofuran-3-ol were introduced into ethanol in a 50 ml flask, and 1 ml of concentrated sulphuric acid was added. The mixture was then heated to reflux for 4 hours. After cooling, 10 ml of water were added, the ethanol was distilled off, and the mixture was extracted with dichloromethane. Washing of the organic phase with sodium bicarbonate solution, drying over sodium sulphate and removal of the solvent in vacuo resulted in 220 mg (80% of theory) of 2-(n-butyl)-5-nitrobenzofuran as yellow oil.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. At least one compound of the formula (II),

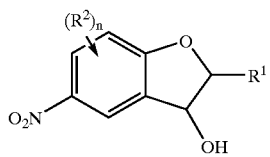

(II)

wherein $R^1$ is hydrogen or $C_1$–$C_{12}$-alkyl, and $R^2$ are in each case independently of one another: fluorine, chlorine, bromine, iodine, $C_1$–$C_{12}$-alkyl, $C_1$–$C_{12}$-alkoxy, hydroxyl, $NR^3R^4$ or $CONR^3R^4$, where $R^3$ and $R^4$ are each, independently of one another, hydrogen or $C_1$–$C_{12}$-alkyl, or $NR^3R^4$ as a whole is a cyclic amino radical having 4 to 12 carbon atoms, COO—($C_1$–$C_{12}$-alkyl), —COO($C_4$–$C_{24}$-aryl), —COO($C_5$–$C_{25}$-arylalkyl), CO($C_1$–$C_{12}$-alkyl), CO($C_4$–$C_{24}$-aryl) or $C_1$–$C_{12}$-fluoroalkyl and n is zero, one, two or three, or in the case where n is two or three it is possible for two adjacent $R^2$ substituents to be part of a fused ring system which in turn may optionally be substituted by the radicals mentioned above for $R^2$.

2. 2-(n-Butyl)-5-nitro-2,3-dihydrobenzofuran-3-ol.

3. A process for preparing at least one compound of formula (I),

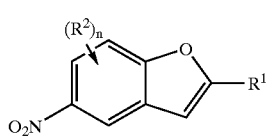

(I)

in which $R^1$ is hydrogen or $C_1$–$C_{12}$-alkyl and $R^2$ are in each case independently:

fluorine, chlorine, bromine, iodine, $C_1$–$C_{12}$-alkyl, $C_1$–$C_{12}$-alkoxy, hydroxyl, $NR^3R^4$ or $CONR^3R^4$, where $R^3$ and $R^4$ are each, independently of one another, hydrogen or $C_1$–$C_{12}$-alkyl, or $NR^3R^4$ as a whole is a cyclic amino radical having 4 to 12 carbon atoms COO-($C_1$–$C_{12}$-alkyl), —COO($C_1$–$C_{24}$-aryl), —COO($C_5$–$C_{25}$-arylalkyl), CO($C_1$–$C_{12}$-alkyl), CO($C_1$–$C_{24}$-aryl) or $C_1$–$C_{12}$-fluoroalkyl and is zero, one, two or three, or An in the case where n is two or three it is possible for two adjacent $R^2$ substituents to be part of a fused ring system which in turn may optionally be substituted by the radicals mentioned above for $R^2$ comprising converting by dehydration
of at least one compound of formula (II)

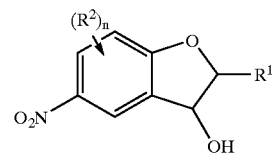

(II)

in which $R^1$, $R^2$ and n have the meaning under formula (I) into at least one compound of formula (I);

wherein at least one compound of the formula (II) is or are obtained by reducing at least one compound of the formula (III)

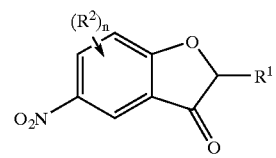

(III)

wherein $R^1$, $R^2$ and n have the meaning specified under formula (I) as indicated above.

4. The process according to claim 3, wherein wherein at least one compound of the formula (III) is or are reduced by aluminium-hydrogen or boron-hydrogen compounds.

5. The process according to claim 3, at least one compound of the formula (III) are obtained by nitrating compounds of the formula (IV)

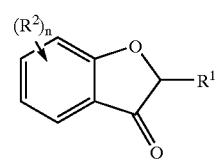

(IV)

in which $R^1$, $R^2$ and n have the meanings specified under formula (I).

6. The process according to claim 5, wherein compounds of the formula (IV) are obtained by hydrolysing at least one compound of the formula (V)

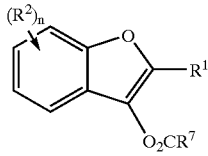
(V)

in which
R$^1$, R$^2$ and n have the meaning specified under formula (I) in claim 3, and
R$^7$ is C$_1$–C$_{12}$-alkyl, C$_5$–C$_{25}$-arylalkyl, C$_4$–C$_{24}$-aryl or C$_1$–C$_{12}$-fluoroalkyl.

7. The process according to claim 6, wherein at least one compound of the formula (V) is or are obtained by cyclizing decarboxylation of compounds of the formula (VI),

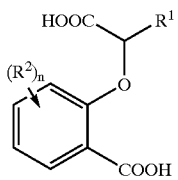
(VI)

in which R$^1$, R$^2$ and n have the meaning specified under formula (I) in claim 3,
in the presence of at least one compound of the formula (RIII)

 R$^7$COR$^8$ (RIII)

in which
R$^7$ has the meaning specified under formula (V), and
R$^8$ is —O$_2$CR$^7$, hydroxyl or OM, where M is an alkaline earth metal or alkali metal.

8. The process according to claim 7, wherein at least one compound of the formula (VI) are obtained by hydrolysing at least one compound of the formula (VII)

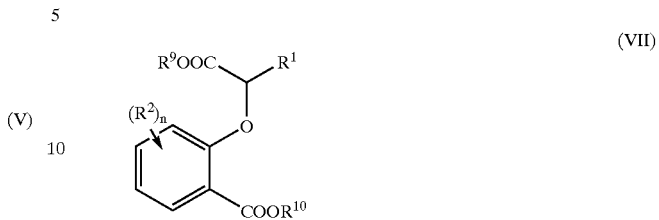
(VII)

in which
R$^1$, R$^2$ and n have the meaning specified under formula (I), and
R$^9$ and R$^{10}$ are each independently of one another hydrogen, C$_1$–C$_{12}$-alkyl, C$_5$–C$_{25}$-arylalkyl or C$_4$–C$_{24}$-aryl.

9. The process according to claim 8, wherein at least one compound formula (VII) are obtained by reacting at least one compound of the formula (VIII)

(VIII)

in which
R$^2$ and n have the meaning specified under formula (I) in claim 3 and
R$^{10}$ has the meaning specified under formula (VII), with at least one compound formula (IX)

(IX)

in which
R$^1$ has the meanings specified under formula (I) in claim 3, and
R$^9$ has the meaning specified under formula (VII), and
X is chlorine, bromine, iodine or R$^{11}$SO$_3$— where
R$^{11}$ is C$_1$–C$_{12}$-alkyl, C$_4$–C$_{24}$-aryl, C$_5$–C$_{25}$-arylalkyl or C$_1$–C$_{12}$-fluoroalkyl.

10. The process according to claim 7, wherein at least one compound of formula (VI) are prepared by reacting at least one compound of formula (VIII) with at least one compound of formula (IX) in a one-pot reaction with hydrolysis of the ester functions taking place simultaneously.

* * * * *